US006781692B1

(12) United States Patent
Rosencwaig

(10) Patent No.: US 6,781,692 B1
(45) Date of Patent: Aug. 24, 2004

(54) METHOD OF MONITORING THE FABRICATION OF THIN FILM LAYERS FORMING A DWDM FILTER

(75) Inventor: Allan Rosencwaig, Danville, CA (US)

(73) Assignee: Therma-Wave, Inc., Fremont, CA (US)

( * ) Notice: Subject to any disclaimer, the term of this patent is extended or adjusted under 35 U.S.C. 154(b) by 214 days.

(21) Appl. No.: 09/939,817

(22) Filed: Aug. 27, 2001

Related U.S. Application Data

(60) Provisional application No. 60/228,476, filed on Aug. 28, 2000.

(51) Int. Cl.[7] ............................ G01J 4/00; G01B 11/06; G01B 9/02; G01V 5/00
(52) U.S. Cl. ..................... 356/369; 356/381; 356/351; 356/364; 250/255; 427/9; 427/10
(58) Field of Search ................................ 356/369, 381, 356/351, 364–368; 250/255, 225; 427/9, 10

(56) References Cited

U.S. PATENT DOCUMENTS

| | | | |
|---|---|---|---|
| 4,999,014 A | | 3/1991 | Gold et al. ............ 356/382 |
| 5,042,951 A | | 8/1991 | Gold et al. ............ 356/369 |
| 5,131,752 A | | 7/1992 | Yu et al. .............. 356/369 |
| 5,354,575 A | * | 10/1994 | Dagenais et al. |
| 5,610,392 A | * | 3/1997 | Nagayama et al. |
| 5,620,556 A | | 4/1997 | Henck ................. 438/8 |
| 5,665,214 A | * | 9/1997 | Iturralde |
| 5,798,837 A | * | 8/1998 | Aspnes et al. |
| 5,835,221 A | * | 11/1998 | Lee et al. |
| 5,900,633 A | * | 5/1999 | Solomon et al. |
| 5,900,939 A | | 5/1999 | Aspnes et al. .......... 356/369 |
| 5,955,139 A | * | 9/1999 | Iturralde |
| 6,085,002 A | | 7/2000 | Qiu et al. ............. 385/52 |

OTHER PUBLICATIONS

G.M.W. Kroesen et al., "Nonintrusive wafer temperature measurement using in situ ellipsometry," *J. Appl. Phys.*, vol. 69, No. 5, Mar. 1, 1991, pp. 3390–3392.

C.T. Yu et al., "Using In Situ Ellipsometry for Film Thickness Endpoint Control," *Semiconductor International*, May 1991, pp. 166–169.

M. Haverlag et al., "Ellipsometric study of silicon surface damage in electron cyclotron resonance plasma etching using $CF_4$ and $SF_6$," *Appl. Phys. Lett.*, vol. 16, No. 24, Dec. 14, 1992, pp. 2875–2877.

M. Haverlag et al., "In situ ellipsometry and reflectometry during etching of patterned surfaces: Experiments and simulations," *J. Vac. Sci. Technol. B.* vol. 10, No. 6, Nov./Dec. 1992, pp. 2412–2418.

N. Blayo et al., "Ultraviolet–visible ellipsometry for process control during the etching of submicrometer features," *J. Opt. Soc. Am. A,* vol. 12, No. 3, Mar. 1995, pp. 591–599.

N. Blayo et al., "New Applications of Ellipsometry for Materials Characterization and VLSI Device Process Control," *The Electrochemical Society Proceedings*, vol. 94–33, pp. 207–216.

S.A. Henck, "In situ real–time ellipsometry for film thickness measurement and control," *J. Vac. Sci. Technol. A,* vol. 10, No. 4, Jul./Aug. 1992, pp. 934–938.

R. W. Collins, "Automatic rotating element ellipsometers: Calibration, operation, and real–time applications," *Rev. Sci. Instrum.*, vol. 61, No. 8, Aug. 1990, pp. 2029–2062.

Copy of U.S. patent application No. 09/575,295, filed May 29, 2000, by inventors Lanhua Wei et al., entitled "Monitoring Temperature and Sample Characteristics Using a Rotating Compensator Ellipsometer," 17 pages of application, and 3 pages of informal drawings.

* cited by examiner

*Primary Examiner*—Frank G. Font
*Assistant Examiner*—Khaled Brown
(74) *Attorney, Agent, or Firm*—Stallman & Pollock LLP

(57) ABSTRACT

A narrow band ellipsometer is used to monitor and control the formation of thin layers in an multilayer, thin film interference filter. Optical interference filters used for DWDM application have a large number of thin layers deposited on a substrate. The thickness of the layers must be precisely controlled. An ellipsometer is used to monitor the deposition process and control the layer formation in situ, on a real time basis.

44 Claims, 1 Drawing Sheet

METHOD OF MONITORING THE FABRICATION OF THIN FILM LAYERS FORMING A DWDM FILTER

PRIORITY

This application claims priority to prior provisional application Serial No. 60/228,476, filed Aug. 28, 2000.

TECHNICAL FIELD

The subject invention relates to optical filters formed by depositing a number of thin layers on a substrate. More specifically, the invention relates to an in situ monitoring approach for accurately controlling the deposition of the layers.

BACKGROUND OF THE INVENTION

In the field of optics, it is know to create wavelength selective filters by depositing multiple thin film layers on a substrate. The layers are typically formed from materials which alternate between high and low indices of refraction. The thickness of each layer is selected to be about one-half wavelength of light at wavelengths that are to be transmitted and about one-quarter wavelength of light at wavelengths that are to be reflected.

Such structures are used in optical communication systems to create Dense Wavelength Division Multiplex (DWDM) filters. DWDM filters are of the Fabry-Perot type with up to 200 dielectric layers deposited on a glass substrate or wafer. The DWDM filters operate around the 1550 nm range and have very narrow and sharp transmission notches or bandwidths. Currently, filters are being produced with bandwidths of 100 GHz (~8 angstroms) and 50 GHz (~4 angstroms) bandwidth. The goal is to reach 25 GHz (~2 angstroms) bandwidth in another year or so. This is important since each time the bandwidth is halved, the number of optical channels that can be multiplexed and demultiplexed is doubled.

To achieve such narrow and sharp bandwidths, the thickness of the Fabry-Perot layers must be controlled with extreme precision, typically about 0.1 angstroms. Currently, this is very difficult to achieve with the result that yields of 100 GHz filters is low and production of 50 GHz filters extremely difficult. In most present systems, the thickness of the layers is controlled by setting deposition parameters, such as time and temperature. It is believed that increased accuracy in the deposition of the layers could be achieved if it was possible to actually measure the thin film thickness as it is being deposited. In this manner, the process can be controlled in real time.

SUMMARY OF THE INVENTION

In accordance with the subject invention, the control of the deposition process is significantly improved by the use of a narrow band off-axis ellipsometer in an integrated closed-loop control system. One suitable ellipsometer is marketed by Therma-Wave as part of its OPTI-PROBE product and identified as the Absolute Ellipsometer (AE). This ellipsometer is described in more detail in U.S. Pat. No. 5,900,939, incorporated herein by reference) and includes a laser for generating a probe beam of radiation. The probe beam is passed through a polarizer and strikes the sample. Changes in the polarization state of the reflected beam are monitored using an analyzer. In the illustrated embodiment, the reflected beam is passed through a fixed polarizer and a rotating compensator (retarder). Other conventional ellipsometric detection arrangements, such as a rotating polarizer or analyzer, could be used.

It has been demonstrated that this ellipsometric system can operate as an integrated metrology tool in a semiconductor process device and can achieve precisions of better than 0.005 angstroms and repeatabilities of better than 0.05 angstroms for thickness measurements. Thus, the ellipsometer can be used to monitor film growth on the filter in real time. The output signals from the ellipsometer could be used, for example, for end point determinations, i.e. to determine when the layer thickness has reached a predetermined level.

To improve sensitivity and minimize uncertainties in the measurement of films transmitting in the 1550 nm range, it may be desirable to use a probe beam having a wavelength in the 1550 nm region or fractions thereof. Various lasers, such as erbium-glass and certain semi-conductor lasers operate in this wavelength regime and may be suitable to generate the probe beam for the ellipsometer.

It has also been demonstrated that a rotating compensator ellipsometer has the capability for simultaneously measuring the temperatures of the sample during deposition to 1° C., thus permitting one to correct for changes in optical parameters with the temperature of deposition and thereby obtain accurate thickness readings. (See, pending application Ser. No. 09/575,295, filed May 19, 2000, also incorporated herein by reference.)

Further objects and advantages will become apparent from the following detailed description, taken in conjunction with the drawings in which:

DETAILED DESCRIPTION OF THE PREFERRED EMBODIMENT

Figure 1:
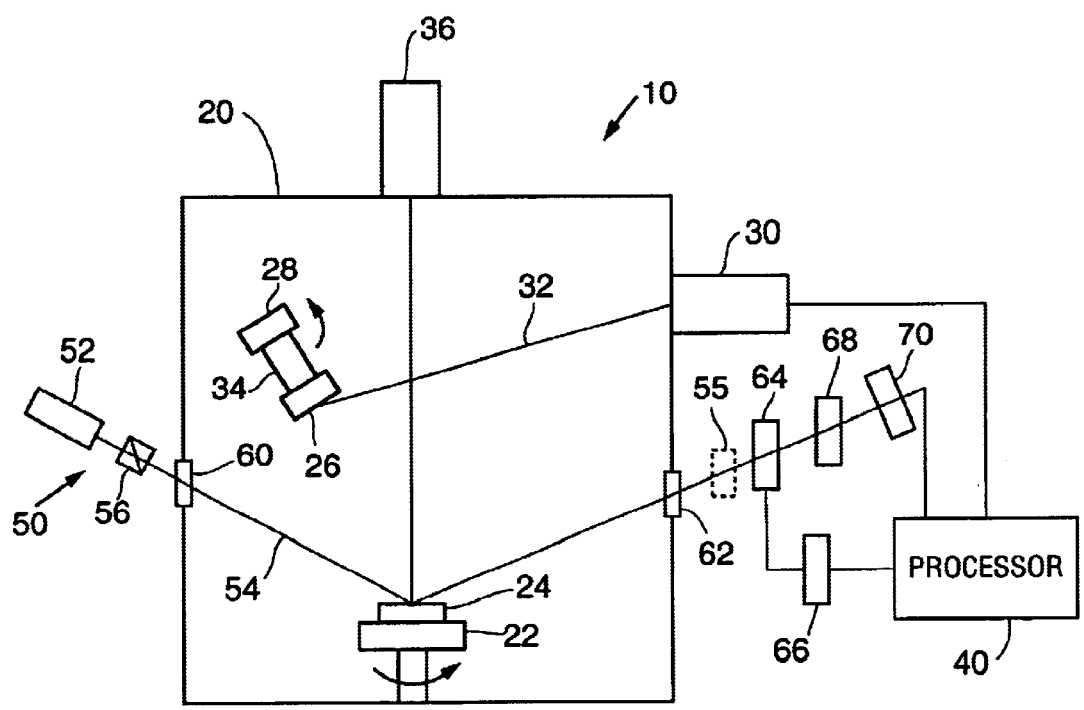
FIG. 1 is a schematic diagram of an integrated deposition and monitoring system for fabricating interference filters.

FIG. 1 illustrates a system 10 formed in accordance with the subject invention. System 10 includes a generic depiction of a deposition chamber 20. A number of commercial vendors sell equipment designed to deposit multiple thin film layers on a substrate. Some of these systems are specifically designed for the manufacture of DWDM filter coatings. Two such vendors are Vacuum Process Technology, Inc (VPT) and Oxford Instruments.

These systems typically include one or more sample stages 22 upon which the substrate 24 (typically glass in a DWDM) rest. The stage may be rotatable to make the deposition layer more uniform. At least two carriers 26, 28 are provided for holding the material which will be used to create the layers. Most multilayer filters are formed from two different material layers, one having a high index of refraction and the other having a low index of refraction. Typical materials used for DWDM fabrication are tantalum and silicon.

The system further includes a mechanism for exciting or bombarding the material in the carriers. Typical mechanisms include e-beam or ion beam sources shown generally at 30. The source generates a beam 32 which will cause the material in the carriers to throw off ions in a sputtering process. The carriers 26, 28 may be selectively movable into the path of the beam, for example, by rotating the carrier support 34, to create pure layers of the one of the two materials. Other approaches are known for creating ions for deposition, including heating the material to a temperature sufficient to cause vaporization.

The system will further include a source 36 of reactive ions, such as oxygen which is directed to the surface of the substrate. The oxygen ions bind to the substrate and to the ions from sputtered material to create, for example, a layer of either tantalum oxide ($Ta_2O_5$) or silicon dioxide ($SiO_2$).

The above system is described only by way of example, and the subject invention is intended to be used with any thin film deposition process suitable for creating DWDM filters.

In the past, the thickness of the layers was primarily controlled by controlling the parameters of these system, for example, the power of the excitation beam, the temperature of the chamber and the length of time the deposition process is to continue. Such parameters can be adjusted through a computer control system 40. After the deposition process was completed, the sample could be tested to determine if the layers were properly deposited. This testing could be performed either destructively or through non-destructive optical means. If the testing demonstrated that the layers were incorrectly deposited, the process parameters could be adjusted during the next run.

As can be appreciated, improved yields could be achieved if the process were monitored in real time, in situ. The subject system addresses this need.

As illustrated in FIG. 1, the system can further include an ellipsometric measurement system 50. In the illustrated embodiment, the system 50 is a rotating compensator ellipsometer. It is within the scope of the subject invention to use other types of ellipsometers such as rotating polarizer or analyzer systems and nulling systems. In addition, although most ellipsometers operate with a beam directed to the sample at an oblique angle (off-axis), those skilled in the art will also recognize that ellipsometric information can be obtained from normal incidence embodiments. Examples of normal incidence ellipsometry also include the systems described in U.S. Pat. Nos. 4,999,014 and 5,042,951, both incorporated herein by reference. Also, although only one rotating compensator is shown, those skilled in the art will understand that systems with two rotating compensators can be used as well.

Ellipsometer 50 includes a light source 52 for emitting a probe beam of radiation 54. Light source 52 is preferably a laser generating a narrowband, wavelength stable output. One possibility for the light source is a gas discharge laser such as a helium neon laser emitting a monochromatic beam at 633 nm. The advantage to a helium neon laser is that it generates a collimated beam of light of a known fixed wavelength which, in an ellipsometer configuration, substantially minimizes alignment, calibration, and measurement problems. It should be noted, however, the subject invention can be implemented with other light sources, including solid state lasers or laser diodes. As discussed in further detail below, there may be some advantages to using a laser with an infrared output.

In addition, light source 52 could be a broad band, polychromatic source such as a tungsten and/or a deuterium bulb. In such a case, the light can be passed through a wavelength selective filter or monochrometer, located either before or after the sample (illustrated in phantom line at 55) to create a narrow wavelength band of light for measurement. Use of a broadband light source and monochrometer (or a spectrometer capable of taking multiple wavelength measurements simultaneously) is desirable if a plurality of data points are necessary or desirable. If only a single data point will suffice, it would be preferable to use a light source which generates a fixed, known, narrow spectral line output such as a gas laser or lamp (for example, a low pressure mercury lamp.)

The probe beam 54 passes through and interacts with a polarizer 56 to create a known polarization state. In the preferred embodiment, polarizer 56 is a linear polarizer made from a quartz Rochon prism, but in general the polarization does not necessarily have to be linear, nor even complete. Polarizer 56 can also be made from magnesium fluoride or calcite. The azimuth angle of polarizer 56 is oriented so that the plane of the electric vector associated with the linearly polarized beam exiting from the polarizer 56 is at a known angle with respect to the plane of incidence (defined by the propagation direction of the beam 54 and the normal to the surface of sample 24). The azimuth angle is preferably selected to be on the order of 30 degrees because the sensitivity is optimized when the reflected intensities of the P and S polarized components are approximately balanced. It should be noted that polarizer 56 can be omitted if the light source 52 emits light with the desired known polarization state.

The beam 54 is directed to sample 24 at an oblique angle. The beam passes into the chamber 20 through a transparent window 60. The beam 54 is ideally incident on sample 24 at an angle of the order of 70 degrees to the normal of the sample surface because sensitivity to sample properties is maximized in the vicinity of the Brewster or pseudo-Brewster angle of a material. Based upon well-known ellipsometric principles, the reflected beam will generally be in a mixed linear and circular polarization state after interacting with the sample, as compared to the linear polarization state of the incoming beam.

The reflected beam 54 passes out of the chamber through window 62 through a rotating compensator (retarder) 64, which introduces a relative phase delay $\delta$ (phase retardation) between a pair of mutually orthogonal polarized optical beam components. The amount of phase retardation is a function of the wavelength, the dispersion characteristics of the material used to form the compensator, and the thickness of the compensator. Compensator 64 is rotated at an angular velocity omega ($\omega$) about an axis substantially parallel to the propagation direction of beam 54, preferably by an electric motor 66. Compensator 64 can be any conventional waveplate compensator, for example those made of crystal quartz. The thickness and material of the compensator 64 are selected such that a desired phase retardation of the beam is induced. In the preferred embodiment, compensator 64 is a bi-plate compensator constructed of two parallel plates of anisotropic (usually birefringent) material, such as quartz crystals of opposite handedness, where the fast axes of the two plates are perpendicular to each other and the thicknesses are nearly equal, differing only by enough to realize a net first-order retardation for the wavelength produced by the light source 52.

Beam 54 then interacts with analyzer 68, which serves to mix the polarization states incident on it. In this embodiment, analyzer 68 is another linear polarizer, preferably oriented at an azimuth angle of 45 degrees relative to the plane of incidence. However, any optical device that serves to appropriately mix the incoming polarization states can be used as an analyzer. The analyzer 68 is preferably a quartz Rochon or Wollaston prism but, as noted above, could also formed from magnesium fluoride or calcite.

The rotating compensator 64 changes the polarization state of the beam as it rotates such that the light transmitted by analyzer 68 is characterized by:

$$I(t) = (1/2)[|E_x|^2(1 + \cos^2(\delta/2) + |E_y|^2 \sin^2(\delta/2)] - \quad (1)$$

$$Im(E_x E_y^*)\sin\delta\sin(2\omega t) +$$

$$Re(E_x E_y^*)\sin^2(\delta/2)\sin(4\omega t) +$$

$$(1/2)(|E_x|^2 - |E_y|^2)\sin2(\delta/2)\cos(4\omega t)$$

$$= a_0 + b_2\sin(2\omega t) + a_4\cos(4\omega t) + b_4\sin(4\omega t),$$

where $E_x$ and $E_y$ are the (complex) components (amplitude and phase) of the projections of the field incident on the polarization-state detector (compensator and analyzer) with the x axis being defined as the polarization plane of the analyzer, $E_x E_y^*$ is the product of $E_x$ and the complex conjugate of $E_y$ which in turn has a real and an imaginary part and which together with the first two intensities gives the relative phase, $\delta$ is the phase retardation of the compensator, and $\omega$ is the angular rotational frequency of the compensator.

For linearly polarized light reflected at non-normal incidence from the specular sample, we have $$E_x = r_p \cos P$$

$$E_y = r_s \sin P \quad (2)$$

where the transmission axis of the analyzer is assumed to be in the plane of incidence, $r_p$ and $r_s$ are the complex (i.e., field) reflectances of the sample being measured (where $r_p$ is for linearly polarized light in the plane of incidence, and $r_s$ is for linearly polarized light perpendicular to the plane of incidence) and P is the azimuth angle of the transmission axis of the polarizer with respect to the plane of incidence. The coefficients $a_0$, $b_2$, $a_4$, and $b_4$ can be combined in various ways to determine the complex reflectance ratio (where $\psi$ and $\Delta$ are the ellipsometric parameters):

$$r_p/r_s = \tan\psi e^{i\Delta}. \quad (3)$$

It should be noted that the compensator 64 can be located either between the sample and the analyzer 68 (as shown in FIG. 1), or between the sample and the polarizer 56, with appropriate and well known minor changes to the equations. It should also be noted that the polarizers and compensator are all optimized in their construction for the specific wavelength of light produced by light source 52, which maximizes the accuracy of ellipsometer.

Beam 54 then enters detector 70, which measures the intensity of the beam passing through the compensator/analyzer combination. The processor 40 processes the intensity information measured by the detector 70 to determine the polarization state of the light after interacting with the analyzer, and therefore the ellipsometric parameters of the sample. This information processing includes measuring beam intensity as a function of the azimuth (rotational) angle of the compensator about its axis of rotation. This measurement of intensity as a function of compensator rotational angle is effectively a measurement of the intensity of beam 54 as a function of time, since the compensator angular velocity is usually known and a constant. As can be seen from equation (1), a rotating compensator will generate a signal having a dc component, a $2\omega$ signal and a $4\omega$ signal with respect to the rotation rate of the compensator.

It should be noted that the compensator need not be continuously rotating, but can be rotated incrementally with measurements being taken at each rotational position to create an effective angular frequency of $\omega$. Even if the compensator is rotated incrementally, the output can still be analyzed in the form of $2\omega$ and $4\omega$ signals.

It is convenient to recast Equation (1) in terms of normalized Fourier coefficients $\beta_2$, $\alpha_4$, and $\beta_4$ defined as $$I = I_0[1+\beta_2 \sin 2\omega t + \alpha_4 \cos 4\omega t + \beta_4 \sin 4\omega t], \quad (4)$$

since these are the coefficients that can be determined most accurately experimentally, e.g., by a normalized harmonic analysis of the detected photoelectric current from detector 70. For our purposes we need only relative intensities, whence it is useful to define a relative amplitude $\tan\psi'$ and a relative phase $\Delta'$ of the two field components such that $\tan\psi' \exp(i\Delta') = E_y/E_x$. In terms of $\psi'$ and $\Delta'$ we have $$\beta_2 = [\sin \Delta' \sin \delta \sin 2\psi']/D;$$

$$\alpha_4 = [\sin^2(\delta/2)\cos 2\psi']/D;$$

$$\beta_4 = [\cos \Delta' \sin^2(\delta/2) \sin 2\psi']/D; \quad (5)$$

where $$D = [1+\cos^2(\delta/2)]\cos^2 \psi' + \sin^2(\delta/2)\sin^2 \psi'.$$

As is well known in the art, the ellipsometric parameters can be used to determine information about the characteristics of a thin film. Narrow band ellipsometry is particularly well suited to provide highly accurate information about layer thickness for very thin layers.

Based on the output signals from the ellipsometer 50, the process parameters of the deposition system can be controlled. In the most simple form, the output signal pattern corresponding to the desired thickness of each layer can be predetermined and stored in the processor's memory. During operation, the processor will monitor the output signals until the predetermined end point signal is reached and the deposition process for that layer can be halted. The latter approach minimizes computation time and can be used in repetitive processes. Significantly, this approach insures that the proper thickness of the layer is achieved even if the process parameters of the chamber are operating slightly out of the intended range resulting in a growth rate that is either faster or slower than expected.

In another monitoring approach, the output signal pattern corresponding to all stages of the deposition process as a function of time can be predetermined and stored. During operation, the processor will monitor the output signals and determine if there is any deviation with the expected time dependent signal. If such a deviation is detected, the operator will be signaled to check for anomalies in the deposition system.

Still another approach would be to operate the deposition system as was done in the prior art, with each layer being deposited in accordance with a predetermine recipe. At the end of each deposition step, the ellipsometer system 50 will measure the layer and determine if its thickness or other properties falls within the desired limitations. This analysis can be performed either by comparing the output signals to predetermined acceptable signals or by performing an ellipsometric analysis on the data. In this manner, the thickness of the each layer can be confirmed before the deposition of the next layer begins.

It is also envisioned that the processor might evaluate the characteristics of the layers in real time using the ellipsometric parameters as the deposition procedure was progressing. If the characteristics of the sample varied in any way from the expected characteristics, the processor could adjust the process parameters of the deposition system, including varying the temperature of the chamber, power of the excitation beam, etc. in order to return the operation to within the desired specifications. To successfully carry out such a real time modification of a process, it may be necessary to incorporate additional measurement tools and combine the data. The processor might be provided with an expert system for evaluating the variations in process parameters and for implementing changes to the process.

Another requirement for tight control of the deposition process is rapid measurements to provide quick close-loop control of the process. In particular, measurements need to be made in less than 100 milliseconds. The rotating compensator ellipsometer discussed above can already provide measurements in ~50 milliseconds and this can be readily improved to 10 milliseconds.

In the preferred embodiment, it may be desirable to select the light source 52 to be a laser having an output wavelength near the desired transmission band of the filter. A great majority of current DWDM systems operate in the 1500 nm range. Lasers are available that generate light output at such a wavelength and include erbium glass and tunable color center lasers. InGaAsP semiconductor lasers can also be fabricated to emit in this wavelength region. It may also be useful to use a light source emitting wavelengths at fixed fractions of the transmission wavelength gap (i.e. 750 nm). Although laser sources are preferred because of the narrow band width, it would also be possible to generate the probe beam from a broad band light source in combination with a narrow band filter.

As noted above, although the subject invention is applicable to a variety of ellipsometers, the rotating compensator system has an advantage in that it can simultaneously provide information about the temperature of the sample. More specifically, a rotating compensator ellipsometer generates both $2\omega$ and $4\omega$ signals. For relatively thin films (less than about 100 Angstroms), it has been observed that the $4\omega$ signal varies in response to the temperature of the sample and is substantially independent of thin film thickness. On the other hand, the $2\omega$ signal varies in response to layer thickness and is substantially independent of temperature. By using the $4\omega$ signal, the temperature of the sample can be determined. The temperature of the sample can be used to determine the refractive index and extinction coefficient of the substrate and with that knowledge, the thin film thickness can be accurately determined using the $2\omega$ signal.

Since the sample in a deposition chamber is often subjected to elevated temperatures, this approach can be used to determine layer thickness without having to allow the sample to cool down. Further details of this approach are described in application Ser. No. 09/575,295, filed May 19, 2000, cited above.

As illustrated in FIG. 1, in most DWDM filter deposition systems, the sample is rotated. An ellipsometric measurement can therefore be affected by any wobble in the sample as it rotates. However, the odd harmonics of the output signals of a rotating element ellipsometer might be used to detect and correct for this wobble. In the case of a rotating compensator system, the two and four omega signals are used for measurements while the three omega and higher odd harmonics could be used to detect wobble and other system problems.

While the subject invention has been described with reference to a preferred embodiment, various changes and modifications could be made therein, by one skilled in the art, without varying from the scope and spirit of the subject invention as defined by the appended claims.

I claim:

1. A method of manufacturing a multilayer, thin film interference filter comprising the steps of:

depositing a plurality of thin film layers on a substrate, the plurality of thin film layers forming a multilayer, thin film interference filter; and monitoring the formation of at least some of the thin film layers during the deposition process, said monitoring step including the steps of:

directing a narrow-band radiation probe beam to reflect off the layers on the substrate;

monitoring the change in polarization state of the probe beam induced by the interaction with the layers and generating output signals in response thereto; and controlling the deposition process be on the monitored output signals.

2. A method as recited in claim 1 wherein the step of controlling the deposition process includes halting the process when the monitored output signals fall outside a predetermined range.

3. A method as recited in claim 1 wherein the step of controlling the deposition process includes varying the deposition process parameters.

4. A method as recited in claim 1 further including the step of evaluating the characteristics of the layers based on the monitored change in polarization state of the probe beam and using the results of the evaluation to control the deposition process.

5. A method as recited in claim 1 wherein step of monitoring the change in polarization state of the beam includes passing the beam through a rotating polarizer.

6. A method as recited in claim 1 wherein step of monitoring the change in polarization state of the beam includes passing the beam through a compensator rotated at an effective angular frequency of $\omega$.

7. A method as recited in claim 6 wherein the output signal include $2\omega$ and $4\omega$ components and wherein said $2\omega$ and $4\omega$ components are used to control the deposition process.

8. A method as recited in claim 1 wherein the probe beam is generated by a laser.

9. A method as recited in claim 8 wherein the laser is a gas discharge laser.

10. A method as recited in claim 8 wherein the laser is a diode laser.

11. A method as recited in claim 1 wherein the probe beam is generated by a filtered broad band light source.

12. An apparatus for fabricating an interference filter defined by multiple thin film layers deposited on a substrate comprising:

means for depositing thin film layers on the substrate in order to form a multilayer, thin film interference filter;

a light source for generating a narrow band probe beam which is directed to reflect off the layers on the substrate;

a optical system for monitoring the change in polarization state of the probe beam induced by interaction with the sample and generating output signals in response thereto; and a control system responsive to the output signals for modifying the operation of the deposition means.

13. An apparatus as recited in claim 12 wherein the control system functions to halt the deposition process when the monitored output signals fall outside a predetermined range.

14. An apparatus as recited in claim 12 wherein the control system functions to vary the deposition process parameters in response to the output signals.

15. An apparatus as recited in claim 12 wherein the control system functions to evaluate the characteristics of the layers based on the monitored change in polarization state of the probe beam and uses the results of the evaluation to control the deposition process.

16. An apparatus as recited in claim 12 wherein the optical system includes a rotating polarizer.

17. An apparatus as recited in claim 12 wherein the optical system includes a compensator rotated at an effective angular frequency of $\omega$.

18. An apparatus as recited in claim 17 wherein the output signals include $2\omega$ and $4\omega$ components and wherein said $2\omega$ and $4\omega$ components are used to control the deposition process.

19. An apparatus as recited in claim 12 wherein the light source is a laser.

20. An apparatus as recited in claim 19 wherein the laser is a gas discharge laser.

21. A method of manufacturing a multilayer, thin film interference filter comprising the steps of:
　depositing a plurality of thin film layers on a substrate, the plurality of thin film layers forming a multilayer, thin film interference filter;
　monitoring the formation of at least some of the thin film layers during the deposition process, said monitoring step including the steps of:
　　generating a probe beam from a broad band light source;
　　directing the probe beam to reflect off the layers on the substrate;
　　monitoring the change in polarization state of at least a narrow wavelength band within the probe beam, said change in polarization state being induced by the interaction with the layers and generating output signals in response thereto; and
　　controlling the deposition process based on the monitored output signals.

22. A method as recited in claim 21 wherein broad band light in the probe beam is filtered either before or after reflecting off the sample and prior to the monitoring step to permit measurement of a narrow wavelength band.

23. A method as recited in claim 22 wherein the filtering is performed by one of a monochrometer and a spectrometer.

24. A method as recited in claim 22 wherein multiple narrow wavelength bands are measured simultaneously.

25. A method as recited in claim 22 wherein the step of controlling the deposition process includes halting the process when the monitored output signals fall outside a predetermined range.

26. A method as recited in claim 22 wherein the step of controlling the deposition process includes varying the deposition process parameters.

27. A method as recited in claim 22 further including the step of evaluating the characteristics of the layers based on the monitored change in polarization state of the probe beam and using the results of the evaluation to control the deposition process.

28. A method as recited in claim 22 wherein step of monitoring the change in polarization state of the beam includes passing the beam through a rotating polarizer.

29. A method as recited in claim 22 wherein step of monitoring the change in polarization state of the beam includes passing the bean through a compensator rotated at an effective angular frequency of $\omega$.

30. A method as recited in claim 29 wherein the output signals include $2\omega$ and $4\omega$ components and wherein said $2\omega$ and $4\omega$ components are used to control the deposition process.

31. A method as recited in claim 1 wherein the probe beam is generated by one of a tungsten or a deuterium bulb.

32. An apparatus for fabricating an interference filter defined by multiple thin film layers deposited on a substrate comprising:
　means for depositing thin film layers on the substrate in order to form a multilayer, thin film interference filter;
　light source means for generating a probe beam of radiation which is directed to reflect off the layers on the substrate;
　a optical system for monitoring the change in polarization state of the probe beam induced by interaction with the sample and generating output signals in response thereto; and
　a control system responsive to the output signals for modifying the operation of the deposition means.

33. An apparatus as recited in claim 32 wherein the light source means is a laser for generating a narrow band output.

34. An apparatus as recited in claim 32 wherein the light source means is a broad band light source which is filtered to permit the optical system to monitor the changes in polarization state at a narrow wavelength region.

35. An apparatus as recited in claim 34 wherein the filtering is performed by one of a monochrometer and a spectrometer.

36. An apparatus as recited in claim 34 wherein the filtering is performed with a spectrometer and multiple narrow wavelength bands are measured simultaneously.

37. An apparatus as recited in claim 32 wherein the control system functions to halt the deposition process when the monitored output signals fall outside a predetermined range.

38. An apparatus as recited in claim 32 wherein the control system functions to vary the deposition process parameters in response to the output signals.

39. An apparatus as recited in claim 32 wherein the control system functions to evaluate the characteristics of the layers based on the monitored change in polarization state of the probe beam and uses the results of the evaluation to control the deposition process.

40. An apparatus as recited in claim 32 wherein the optical system includes a rotating polarizer.

41. An apparatus as recited in claim 32 wherein the optical system includes a compensator rotated at an effective angular frequency of $\omega$.

42. An apparatus as recited in claim 41 wherein the output signals include $2\omega$ and $4\omega$ components and wherein said $2\omega$ and $4\omega$ components are used to control the deposition process.

43. A method of manufacturing a multilayer, thin film interference filter comprising the steps of:
　depositing a plurality of thin film layers on a substrate, the plurality of thin film layers formed from materials alternating between high and low indices of refraction;
　monitoring the formation of each of the plurality of thin film layers during the deposition process, said monitoring step including the steps of:
　　directing a narrow-band radiation probe beam to reflect off the layers on the substrate;
　　monitoring the change in polarization state of the probe beam induced by the interaction with the layers in order to determine layer thickness, and generating output signals in response thereto; and
　　controlling the deposition process based on the generated output signals.

44. A method of manufacturing a multilayer, thin film interference filter comprising the steps of:
　depositing a plurality of thin film layers on a substrate, the plurality of thin film layers formed from materials alternating between high and low indices of refraction;

monitoring the formation of each of the plurality of thin film layers during the deposition process, said monitoring step including the steps of:
  directing a narrow-band radiation probe beam to reflect off the layers on the substrate;
  monitoring the change in polarization state of the probe beam induced by the interaction with the layers in order to determine layer thickness and temperature, and generating output signals in response thereto; and
controlling the deposition process based on the generated output signals.

* * * * *